US011219632B2

(12) United States Patent
Shinzato et al.

(10) Patent No.: US 11,219,632 B2
(45) Date of Patent: Jan. 11, 2022

(54) SKIN PIGMENTATION INHIBITOR

(71) Applicant: Oriental Yeast Co., Ltd., Tokyo (JP)

(72) Inventors: Tatsuya Shinzato, Nagahama (JP); Tetsuro Enomoto, Tokyo (JP); Hisataka Yasuda, Nagahama (JP); Hideo Arai, Tokyo (JP)

(73) Assignee: ORIENTAL YEAST CO., LTD., Tokyo (JP)

( * ) Notice: Subject to any disclaimer, the term of this patent is extended or adjusted under 35 U.S.C. 154(b) by 72 days.

(21) Appl. No.: 16/484,004

(22) PCT Filed: Feb. 8, 2018

(86) PCT No.: PCT/JP2018/004459
§ 371 (c)(1),
(2) Date: Aug. 6, 2019

(87) PCT Pub. No.: WO2018/147385
PCT Pub. Date: Aug. 16, 2018

(65) Prior Publication Data
US 2020/0016183 A1    Jan. 16, 2020

(30) Foreign Application Priority Data
Feb. 8, 2017   (JP) .............................. JP2017-020921

(51) Int. Cl.
*A61K 31/706* (2006.01)
*A61K 8/60* (2006.01)
*A61K 9/00* (2006.01)
*A61P 17/00* (2006.01)
*A61Q 19/02* (2006.01)

(52) U.S. Cl.
CPC ............. *A61K 31/706* (2013.01); *A61K 8/60* (2013.01); *A61K 9/0053* (2013.01); *A61P 17/00* (2018.01); *A61Q 19/02* (2013.01)

(58) Field of Classification Search
CPC ........... A61P 17/00; A61Q 19/02; A61K 8/60; A61K 31/706; A61K 9/0053
USPC .......................................................... 514/43
See application file for complete search history.

(56) References Cited

U.S. PATENT DOCUMENTS

| | | | |
|---|---|---|---|
| 7,737,158 B2 | 6/2010 | Imai et al. | |
| 10,695,360 B2 * | 6/2020 | Yoshino | ............... A61K 31/197 |
| 2007/0082373 A1 | 4/2007 | Imai et al. | |
| 2013/0018020 A1 | 1/2013 | Shin et al. | |

FOREIGN PATENT DOCUMENTS

| | | | | |
|---|---|---|---|---|
| CN | 104771330 | | 7/2015 | |
| CN | 104771330 A | * | 7/2015 | ............... A61K 8/60 |
| EP | 1378224 | | 1/2004 | |
| EP | 3682746 | | 7/2020 | |
| JP | 2004-217629 | | 8/2004 | |
| JP | 2004-217629 A | * | 8/2004 | ........... A61K 31/197 |
| JP | 2004217629 | * | 8/2004 | |
| JP | 2010-174049 | | 8/2010 | |
| JP | 4614886 | | 1/2011 | |
| JP | 2013-523721 | | 6/2013 | |
| JP | 2013-523721 A | * | 6/2013 | ............... A61K 8/44 |
| JP | 2013523721 | * | 6/2013 | |
| JP | 2016-135750 | | 7/2016 | |
| JP | 2016-135750 A | * | 7/2016 | ............... A61K 8/60 |
| KR | 10-2016-0047914 | | 5/2016 | |
| WO | 2014/146044 | | 9/2014 | |

OTHER PUBLICATIONS

International Search Report of PCT/JP2018/004459, dated Apr. 10, 2018, 3 pages, with English translation.
Roider E et al.: "571 Identifying a novel mechanism of human skin pigmentation", Journal of Investigative Dermatology; 49th Annual ESDR Meeting Sep. 18, 2019 to Sep. 21, 2019 Bordeaux, Elsevier, NL, vol. 139, No. 9, Supplement, Sep. 1, 2019 (Sep. 1, 2019), p. S313, XP009523054, ISSN: 0022-202X, DOI: 10.1016/J.JID.2019.07.575.
The extended European search report issued for 18751524.2, dated Oct. 2, 2020, 10 pages.

* cited by examiner

*Primary Examiner* — Ganapathy Krishnan
(74) *Attorney, Agent, or Firm* — Hamre, Schumann, Mueller & Larson, P.C.

(57) ABSTRACT

An object of the present invention is to provide a material which can be safely ingested and which inhibits skin pigmentation. Therefore, the invention is a skin pigmentation inhibitor, containing a β-nicotinamide mononucleotide or a pharmaceutically acceptable salt thereof; and a solvate thereof as an active ingredient; a health supplement which contains the skin pigmentation inhibitor and is ingested to inhibit skin pigmentation; and a method for inhibiting skin pigmentation, including ingesting the skin pigmentation inhibitor.

3 Claims, 1 Drawing Sheet

SKIN PIGMENTATION INHIBITOR

TECHNICAL FIELD

The present invention relates to a material for inhibiting skin pigmentation, a skin pigmentation inhibitor containing the material as an active ingredient, and a method for inhibiting skin pigmentation using the material.

Priority is claimed on Japanese Patent Application No. 2017-020921, filed Feb. 8, 2017, the content of which is incorporated herein by reference.

BACKGROUND ART

When the skin is stimulated due to ultraviolet irradiation, a melanin pigment is produced to protect skin cells from ultraviolet. The produced melanin pigment absorbs ultraviolet, thereby preventing ultraviolet from penetrating deep into the skin. As described above, the melanin pigment is an important pigment for protecting skin cells, but if it is excessively produced, it is deposited on the skin and becomes a cause of stains and freckles. Stains and freckles tend to be avoided from the viewpoint of beauty, and consumers are highly interested in skin whitening agents, and thus there is also active development of ingredients having a whitening effect that inhibits the deposition of a melanin pigment on the skin. For example, it has been reported that nicotinamide has an effect of inhibiting an increase of melanocytes due to ultraviolet irradiation, and by orally ingesting nicotinamide, it is possible to prevent pigmentation and inhibit further deterioration of stains and freckles by ultraviolet irradiation (refer to, for example, Patent Literature 1).

Nicotinamide mononucleotide (NMN) is a biosynthetic intermediate metabolite of the coenzyme $NAD^+$. In recent years, it has been reported that NMN exhibits an effect of ameliorating an insulin secretory ability in senescent mice, exhibits an effect of drastically ameliorating insulin sensitivity and secretion in a mouse model with type 2 diabetes caused by a high-fat diet and aging (refer to, for example, Patent Literature 2), and exhibits an effect of significantly enhancing a mitochondrial function of aged muscle. In addition, it has been reported that administration of NMN is useful for ameliorating or preventing symptoms of various age-related diseases such as obesity, elevated blood lipid levels, decreased insulin sensitivity, decreased memory ability, and ocular function deterioration such as macular degeneration (refer to, for example, Patent Literature 3). Furthermore, it has been reported that cosmetic products such as lotions containing NMN are less stimulative to the skin, and exhibit an effect of preventing or ameliorating rough skin (refer to, for example, Patent Literature 4) and an effect of accelerating collagen production (refer to, for example, Patent Literature 5).

CITATION LIST

Patent Literature

[Patent Literature 1]
 Japanese Unexamined Patent Application, First Publication No. 2010-174049
[Patent Literature 2]
 U.S. Pat. No. 7,737,158
[Patent Literature 3]
 PCT International Publication No. WO2014/146044
[Patent Literature 4]
 Japanese Unexamined Patent Application, First Publication No. 2016-135750
[Patent Literature 5]
 Japanese Patent No. 4614886

SUMMARY OF INVENTION

Technical Problem

An object of the present invention is to provide a material which can be safely ingested and which inhibits skin pigmentation.

Solution to Problem

As a result of intensive studies to achieve the above object, the inventors of this invention have found that 3-nicotinamide mononucleotide (β-NMN) has an effect of inhibiting skin pigmentation, and therefore have completed the invention.

Therefore, the present invention provides the following skin pigmentation inhibitor, a health supplement, and a method for inhibiting skin pigmentation.
[1] A skin pigmentation inhibitor, containing, as an active ingredient: a β-NMN or a pharmaceutically acceptable salt thereof; and a solvate thereof.
[2] The inhibitor according to [1], which is orally administered.
[3] A health supplement which contains the inhibitor according to [1] or [2] and is ingested to inhibit skin pigmentation.
[4] A method for inhibiting skin pigmentation, comprising ingesting the inhibitor according to [1] or [2].
[5] The inhibitor according to [1], which is transdermally administered.
[6] A cosmetic product which contains the inhibitor according to [1] or [5] and is brought into contact with skin to inhibit skin pigmentation.
[7] A method for inhibiting skin pigmentation, comprising bringing the inhibitor according to [1] or [5] into contact with skin.

Advantageous Effects of Invention

The skin pigmentation inhibitor according to the present invention contains β-NMN, which is originally present in a living body, as an active ingredient, and can inhibit skin pigmentation such as melanin caused by ultraviolet, other skin stimulation, and the like. For this reason, the skin pigmentation inhibitor of the invention can be safely ingested without causing side effects, inhibits skin pigmentation, and thus is useful for preventing or ameliorating skin stains associated with the pigmentation.

DESCRIPTION OF EMBODIMENTS

Figure 1:
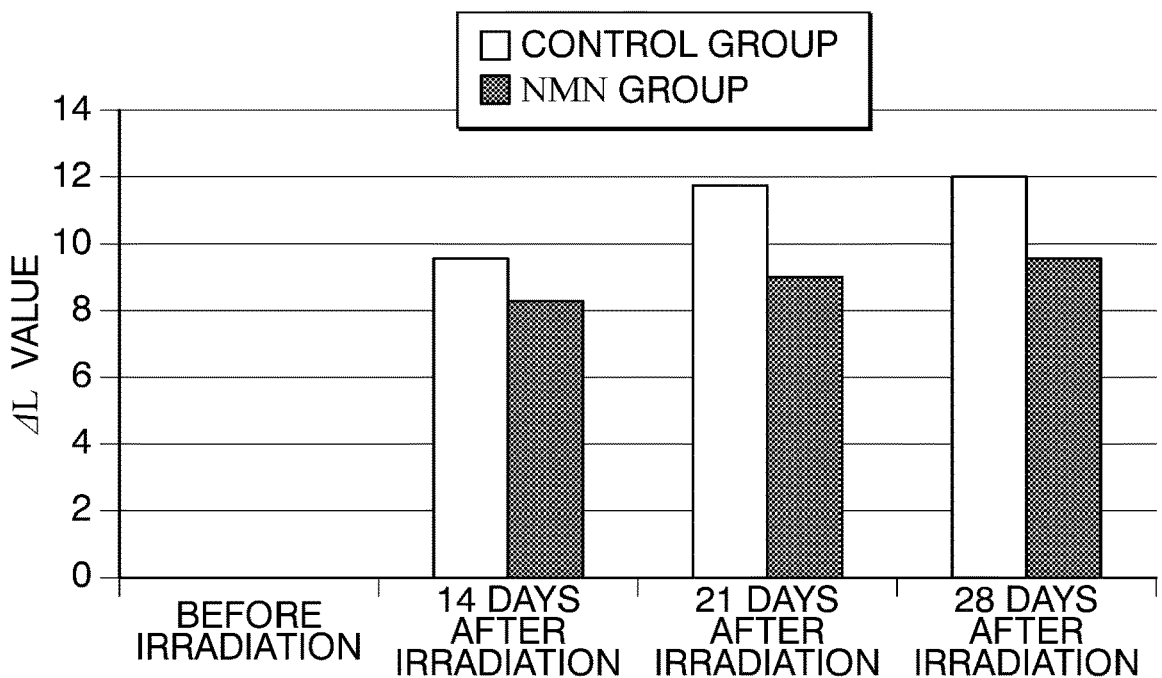
FIG. 1 is a graph showing an amount of change in an L value (ΔL value) at an ultraviolet irradiation site for each guinea pig in a group (NMN group) to which β-NMN is administered and a group (control group) to which water for injection is administered in Example 1.

A skin pigmentation inhibitor of the present invention (hereinafter also referred to as the "pigmentation inhibitor of the invention") contains NMN (chemical formula: $C_{11}H_{15}N_2O_8P$) as an active ingredient. By ingesting NMN, it is possible to inhibit skin pigmentation caused by ultraviolet, other skin stimulation, and the like. For this reason, the pigmentation inhibitor of the invention is suitable as an active ingredient of a whitening composition which is ingested for the purpose of preventing or ameliorating skin darkening, stains, freckles, and the like due to melanin pigmentation, and particularly, for the purpose of preventing or ameliorating pigmentation due to ultraviolet irradiation.

Regarding NMN, two types of α and β are present as optical isomers, but NMN, which is used as the active ingredient of the pigmentation inhibitor of the invention, is β-NMN (CAS number: 1094-61-7). A structure of β-NMN is shown below.

[Chem. 1]

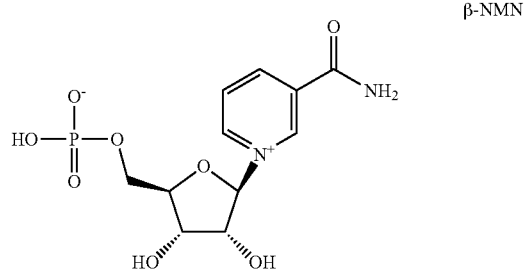

β-NMN

β-NMN that is an active ingredient may be prepared by any method. For example, β-NMN obtained by purifying β-NMN artificially synthesized by a chemical synthesis method, an enzymatic method, a fermentation method, or the like can be used as the active ingredient. In addition, because β-NMN is a component widely present in a living body, β-NMN obtained by extraction and purification from natural raw materials such as animals, plants, and microorganisms can also be used as the active ingredient. Furthermore, commercially available purified β-NMN may be used.

As a chemical method for synthesizing β-NMN, for example, β-NMN can be produced by reacting nicotinamide with L-ribose tetraacetate, and phosphorylating the obtained nicotinamide mononucleotide. As an enzymatic method, for example, β-NMN can be produced from nicotinamide and 5'-phosphoribosyl-1'-pyrophosphate (PRPP) by nicotinamide phosphoribosyltransferase (NAMPT). As a fermentation method, for example, β-NMN can be produced from nicotinamide using a metabolic system of a microorganism expressing NAMPT.

The active ingredient of the pigmentation inhibitor of the invention may be pharmaceutically acceptable salts of β-NMN. The pharmaceutically acceptable salt of β-NMN may be an inorganic acid salt or an organic acid salt having a basic site such as an amine. Examples of acids constituting such acid salts include acetic acid, benzenesulfonic acid, benzoic acid, camphorsulfonic acid, citric acid, ethenesulfonic acid, fumaric acid, gluconic acid, glutamic acid, hydrobromic acid, hydrochloric acid, isethionone acids, lactic acid, maleic acid, malic acid, mandelic acid, methanesulfonic acid, mucic acid, nitric acid, pamoic acid, pantothenic acid, phosphoric acid, succinic acid, sulfuric acid, tartaric acid, p-toluenesulfonic acid, and the like. The pharmaceutically acceptable salt of β-NMN may be an alkali salt or an organic salt having an acidic site such as a carboxylic acid. Examples of bases constituting such acid salts include bases which are alkali metal salts or alkaline earth metal salts and which are induced from bases such as sodium hydride, potassium hydroxide, calcium hydroxide, aluminum hydroxide, lithium hydroxide, magnesium hydroxide, zinc hydroxide, ammonia, trimethyl ammonia, triethyl ammonia, ethylene diamine, lysine, arginine, ornithine, choline, N,N'-dibenzyl ethylenediamine, chloroprocaine, procaine, diethanolamine, N-benzylphenethylamine, diethylamine, piperazine, tris(hydroxymethyl)-aminomethane, and tetramethyl ammonium hydroxide.

The active ingredient of the inhibitor of the invention may be a solvate of free β-NMN or pharmaceutically acceptable salts of β-NMN. Examples of solvents that form the above-mentioned solvate include water, ethanol, and the like.

The pigmentation inhibitor of the invention may contain other active ingredients in addition to β-NMN. The other active ingredients are not particularly limited as long as they do not impair a pigmentation inhibitory effect of β-NMN. Examples of other active ingredients include pigmentation inhibitors other than β-NMN, functional materials having effects other than a pigmentation inhibitory effect, and the like. Examples of pigmentation inhibitors other than β-NMN include nicotinamide, ascorbic acid, kojic acid, arbutin, cysteine, vitamin E, ellagic acid, tranexamic acid, linoleic acid, placenta extract, and the like. Examples of functional materials having effects other than a pigmentation inhibitory effect include taurine, glutathione, carnitine, creatine, coenzyme Q, glucuronic acid, glucuronolactone, capsicum extract, ginger extract, cacao extract, guarana extract, garcinia extract, theanine, γ-aminobutyric acid, capsaicin, capsiate, various organic acids, flavonoids, polyphenols, catechins, xanthine derivatives, indigestible oligosaccharides such as fructooligosaccharides, polyvinylpyrrolidone, and the like.

The pigmentation inhibitor of the invention may consist only of the active ingredient or may contain other ingredients. For example, the inhibitor of the invention can be formulated into various dosage forms by combining the active ingredient with a nontoxic pharmaceutical carrier by conventional means for formulation. Among dosage forms of the inhibitor of the invention, examples of orally administered agents include solid agents such as tablets, granules, powders, capsules, and soft capsules; liquid agents such as solutions, suspensions, and emulsions; lyophilized formulations; and the like. Examples of parenterally administered agents include suppositories, percutaneous absorption agents, inhalants, transnasal agents, enteral agents, and the like in addition to injections. Dosage forms of these parenterally administered agents are not particularly limited, and it is possible to use various dosage forms generally used. For example, as percutaneous absorption agents, a solution, a gel, an ointment, a spray, and the like are preferable.

In the case of orally administered agents and injections, examples of nontoxic carriers/auxiliary agents for pharmaceuticals used for formulation include sugars such as glucose, lactose, sucrose, fructose, and reduced maltose; carbohydrates such as starch, hydroxyethyl starch, dextrin, β-cyclodextrin, crystalline cellulose, and hydroxypropyl cellulose; sugar alcohols such as mannitol, erythritol, sorbitol, and xylitol; esters such as fatty acid glycerides and polyoxyethylene sorbitan fatty acid esters; polyethylene glycol; ethylene glycol; amino acids; albumin; casein; silicon dioxide; water; physiological saline; and the like. In the formulation of the pigmentation inhibitor of the invention, it is possible to appropriately add commonly used additives such as stabilizers, lubricants, wetting agents, emulsifiers, suspending agents, binders, disintegrants, solvents, solubilizers, buffers, tonicity agents, preservatives, flavoring agents, and coloring agents, if required for formulation.

Furthermore, examples of nontoxic carriers/auxiliary agents for pharmaceuticals which are used for formulation and are used in the case of transdermal administration generally include components used for transdermal agents and external skin preparations, such as hydrocarbon oils such as liquid oils and fats, solid oils and fats, waxes, liquid paraffin and squalene, and vaseline, higher fatty acids, higher alcohols, esters, silicones, various surfactants (anionic surfactants, cationic surfactants, amphoteric surfactants, and nonionic surfactants), moisturizer, water-soluble polymer, thickeners, film agents, ultraviolet absorbers, metal ion sequestering agents, lower alcohols, polyhydric alcohols, sugar, amino acid, polymer emulsion, pH adjuster, vitamin, antioxidant, perfume, water, and the like.

The pigmentation inhibitor of the invention is preferably administered to humans and animals other than humans. Examples of animals other than humans include mammals such as cows, pigs, horses, sheep, goats, donkeys, monkeys, dogs, cats, rabbits, mice, rats, hamsters, and guinea pigs. The inhibitor of the invention is preferably administered to and ingested by humans, livestock, laboratory animals, and pets, and is more preferably administered to and ingested by humans.

An administration and ingestion amount of the pigmentation inhibitor of the invention is appropriately selected and determined according to the species of animals to be administered, age, body weight, skin condition, symptoms, degree of disease, administration schedule, formulation form, and the like. For example, in a case of oral administration and ingestion, the pigmentation inhibitor can be administered in one or several doses so that a daily dose per adult is 0.1 mg to 50 g, is preferably 0.5 mg to 35 g, is more preferably 10 mg to 25 g, and is even more preferably 100 mg to 10 g in terms of an amount of β-NMN. In the case of transdermal administration, the pigmentation inhibitor can be brought into contact with (applied, sprayed, dipped, and the like) the skin once or several times so that a daily dose per $cm^2$ of adult skin is 0.01 to 10 mg, is preferably 0.02 to 5 mg, and is more preferably 0.05 to 1 mg in terms of an amount of β-NMN.

Because β-NMN is a component that makes up living organisms and is a component contained in foods, it is highly safe and suitable for continuous ingestion for a long period of time. Accordingly, the pigmentation inhibitor of the invention can be used as an active ingredient of a health supplement to be ingested to inhibit skin pigmentation, and of a cosmetic product which is brought into contact with the skin to inhibit skin pigmentation. Health supplements are foods and beverages for supplementing nutrition for the purpose of maintenance or improvement of health conditions, and include foods for specified health use, nutritive function foods, and health foods.

The health supplement according to the present invention can be manufactured by adding a suitable auxiliary to β-NMN and the like, and then forming it into an edible form such as powders, granules, granules, tablets, capsules, soft capsules, pastes, and the like by using commonly used means. The health supplement of the invention may be provided for food as it is, or may be provided for food in a state of being mixed with various foods and beverages. For example, powdered health supplements can be ingested in a state of being dissolved or dispersed in a beverage such as water, alcoholic beverages, fruit juice, milk, and soft drinks. Animals may ingest a feed of the invention as it is, or animals may ingest the feed which is in a state of being mixed with other solid feed or drinking water.

The health supplement of the invention can contain other food ingredients and various additives. Food ingredients include vitamins, carbohydrates, proteins, lipids, dietary fibers, fruit juices, and the like. Specific examples thereof include vitamin B groups such as vitamin $B_1$ derivatives, vitamin $B_2$, vitamin $B_6$, vitamin $B_{12}$, vitamin $B_{13}$, biotin, pantothenic acid, nicotinic acid, and folic acid; fat-soluble vitamins such as vitamin E, vitamin D or derivatives thereof, vitamin $K_1$, vitamin $K_2$, and β-carotene; minerals such as calcium, potassium, iron, and zinc; yeast; L-carnitine; creatine; α-lipoic acid; glutathione; glucuronic acid; taurine; collagen; soy isoflavone; lecithin; peptide; amino acids; γ-aminobutyric acids; diacylglycerol; DHA; EPA; capsaicin; chondroitin sulfate; agaricus persimmon extract; carrot extract; garlic extract; green juice; lecithin; royal jelly; propolis; octacosanol; flavangenol; pycnogenol; maca; chitosan; garcinia extract; chondroitin; glucosamine; and the like. Examples of additives include sweetening agents, acidulants such as organic acids, stabilizers, flavors, coloring agents, and the like.

A cosmetic product according to the present invention can be manufactured by adding appropriate and common components for cosmetic products to β-NMN and the like, and forming it into forms suitable for cosmetic products, for example, forms such as lotion, milk, gel, cream, spray, and the like by using commonly used means. The cosmetic product containing β-NMN can be formed into forms impregnated with cotton, nonwoven fabric, cloth, or the like. Examples of components to be added to the cosmetic product of the invention include moisturizers, thickeners, various surfactants, liquid oils and fats, solid oils and fats, chelating agents, lower alcohols, polyhydric alcohols, sugars, amino acids, polymers emulsions, pH adjusters, antioxidants, preservatives, thickeners, ultraviolet absorbers, perfumes, coloring agents, and the like. In the cosmetic product of the invention, it is possible to add or blend materials generally blended in cosmetic products as an active ingredient, such as various vitamins such as vitamin C and derivatives thereof, vitamin B group, vitamin E and derivatives thereof; cysteine; tyrosinase; hydroquinone; arbutin; placenta; tranexamic acid; retinoic acid; kojic acid; rucinol; ellagic acid; fullerene; coenzyme Q10; astaxanthin; and the like.

EXAMPLES

The present invention will be described in more detail by showing examples, but the invention is not limited to the following examples.

[Brown Guinea Pig]

Brown guinea pigs (Kw1: line A-1, supplied from Kiwa Laboratory Animals Co., Ltd.) used for the subsequent experiment were bred under SPF environment throughout the entire experimental period. As in a case of humans, it is known that pigmentation of the brown guinea pigs of Kw1: line A-1 is caused by ultraviolet irradiation.

Solid feed (LRC4, Oriental Yeast Co., Ltd.) and drinking water were freely ingested throughout the entire experiment period.

[Ultraviolet Irradiation of Brown Guinea Pigs]

Ultraviolet irradiation of the brown guinea pigs was performed as follows.

First, an unanesthetized brown guinea pig was fixed on a fixed plate in an abdominal position, and the back skin was sheared with an electric hair clipper and shaved with an electric shaver. Among the shaved area of the back skin, a region obtained by cutting out a region corresponding to the irradiation site by attaching a tape for bookbinding to an adhesive fabric stretchable bandage (ELASTOPORE No. 50, Nichiban Co., Ltd.) was attached on a site other than the ultraviolet irradiation site, and thereby the region other than the radiation site was light-shielded. Further, the eyes of the guinea pig were also light-shielded from ultraviolet by attaching lint cloth with the adhesive fabric stretchable bandage. Thereafter, ultraviolet (UVB) irradiation was performed from a distance of 40 cm using five SE lamps (wavelength of 250 to 350 nm, FL20S E, Toshiba Corporation) attached to an ultraviolet irradiation apparatus (Y-798-II, Orion Electric Co., Ltd.).

[Measurement of Minimum Erythema Dose]

A minimum erythema dose of the brown guinea pig (the shortest ultraviolet irradiation time that causes erythema on the skin) was measured as follows.

First, a total of six sites, that is, three sites of a 2 cm×2 cm square of the ultraviolet irradiation site were respectively provided symmetrically on the back skin of one brown guinea pig with a middle line sandwiched therebetween, and ultraviolet irradiation was performed according to the above-mentioned ultraviolet irradiation method. An irradiation time was set to 8, 10, 12, 14, 16, and 18 minutes, and a skin reaction at the irradiation site was observed the following day according to the following evaluation standards.

As to another brown guinea pig, an irradiation time was set at 15-second intervals (eight irradiation sites were provided in the same manner as that of the above-described brown guinea pig) between the shortest time at which a skin reaction was observed and the longest time at which a skin reaction was not observed, a skin reaction was observed in the same manner, and the shortest time at which the skin reaction was observed was used as the minimum erythema dose. As a result, the minimum erythema dose was 12 minutes and 15 seconds.

TABLE 1

| Degree of skin reaction | Grade |
| --- | --- |
| Formation of erythema and eschar | |
| No erythema | 0 |
| Very mild degree of erythema (barely recognizable degree) | 1 |
| Visible erythema | 2 |
| Moderate to high degree of erythema | 3 |
| High degree of scarlet-colored erythema and formation of mild degree of eschar (damage in deep part) | 4 |

[Oral Administration]

Regarding oral administration, a solution in which β-NMN (Oriental Yeast Co., Ltd.) was dissolved in injection water (Otsuka Pharmaceutical Factory, Inc.) was orally administered forcedly using a disposable syringe made of polypropylene (Terumo Corporation) attached with a catheter (a nutrition catheter manufactured by JMS Co., Ltd.). At the time of administration, the mixture was stirred using a touch mixer to check that the β-NMN solution did not precipitate. A dosage was calculated from a body weight value on an administration day or a day close to the administration day, and the dosage was 5 mL/kg.

Example 1

Effects of R-NMN on pigmentation induced by ultraviolet were examined using brown guinea pigs.

(Administration of β-NMN)

First, six brown guinea pigs were divided into a group administered β-NMN (NMN group) and a group administered injection water (control group). A day performed this group dividing was considered day 0 of administration, and from the next day, the β-NMN solution or injection water was orally administered to the guinea pigs of each group once a day for 42 days. The β-NMN solution was administered at a dosage of 500 mg/kg body weight.

(Ultraviolet Irradiation)

Ultraviolet irradiation was performed on the guinea pigs in each group a total of three times, on a day after 15 days (first irradiation day) from the administration of β-NMN (injection water for the control group), and on days after 2 and 4 days therefrom. The ultraviolet irradiation of the guinea pig was performed according to the aforementioned method except that skin was shaved the day before ultraviolet irradiation, and one site of a 2 cm×2 cm square among right and left regions on the back skin of the guinea pig with a middle line sandwiched therebetween was used as an ultraviolet irradiation site. An irradiation time was set to the minimum erythema dose (12 minutes and 15 seconds). On the day of ultraviolet irradiation, β-NMN was administered after the irradiation.

(Measurement of pigmentation) L values (brightness) of the skin of the ultraviolet irradiation site of each guinea pig were measured by using Chroma Meter (CR-300, Konica Minolta, Inc.) on the first irradiation day (day 0), and on days 14, 21, and 28. A total of five corners were measurement sites, which are the center of the irradiation site and four corners of diagonal lines, and an average value was used as the L value of each individual. On days 0, 14 and 21, L values were measured before the ultraviolet irradiation, and on day 28, L values were measured in the morning.

Each guinea pig was shaved with an electric hair clipper and an electric shaver every three days or every four days from the first administration. On the L value measurement day, the ultraviolet irradiation site was shaved with an electric hair clipper and an electric shaver before measurement.

ΔL value ([L value before ultraviolet irradiation on first irradiation day]−[L value on observation day]) was calculated from the measured L values.

(Photographing)

One example of each group was photographed after measurement of the L values by a digital camera.

(Weight Measurement)

A body weight of each guinea pig was measured with an electronic balance in the morning once a week from the first administration day. The measurement was performed before the irradiation on the irradiation day, and before the administration on the β-NMN administration day.

(Results)

The ΔL values of each group are shown in FIG. 1, and the body weight are shown in Table 2. As a result, there was no significant difference in body weight in both groups. The ΔL value of the ultraviolet radiation site was checked to be smaller in the NMN group than that in the control group. More specifically, the ΔL value of the control group was 9.47 on day 14, was 11.71 on day 21, and was 12.01 on day 28.

This shows that, by the ultraviolet irradiation, the ΔL value rapidly decreased from day 14, and pigmentation proceeded. The ΔL value of the NMN group was 8.28 on day 14, was 8.99 on day 21, and was 9.55 on day 28. This shows that the pigmentation was inhibited as compared to the control group. Based on these results, it was confirmed that oral administration of β-NMN can inhibit pigmentation due to ultraviolet irradiation.

TABLE 2

| Days after first administration (days) | Control group (g) | NMN group (g) |
| --- | --- | --- |
| 0 | 405 ± 15 | 405 ± 22 |
| 1 | 408 ± 13 | 408 ± 23 |
| 8 | 444 ± 22 | 431 ± 23 |
| 15 | 462 ± 24 | 462 ± 33 |
| 22 | 497 ± 26 | 497 ± 34 |
| 29 | 531 ± 27 | 529 ± 29 |
| 36 | 555 ± 32 | 551 ± 35 |
| 43 | 595 ± 32 | 584 ± 33 |

Example 2

Effects of β-NMN on pigmentation induced by ultraviolet were examined using brown guinea pigs.

(External Preparation)

Ethanol (lot number: DSM5187, Wako Chemical Co., Ltd.), 1,3-butanediol (lot number: TWQ 6672, Wako Pure Chemical Industries, Ltd.), and injection water (lot number: K5F71, Otsuka Pharmaceutical Factory, Inc.) were mixed at a ratio of 1:1:8 (a volume ratio), and used as a solvent. A solution dissolved β-NMN in this solvent at a concentration of 0.5% by mass was used as a β-NMN-containing external preparation.

(Administration of β-NMN)

First, six brown guinea pigs were divided into a group orally administered β-NMN and a group not administered β-NMN. In the group orally administered β-NMN, the same β-NMN solution in Example 1 was orally administered, and by dividing application sites of each individual, the group was divided into a group to which only the solvent of the external preparation was transdermally administered (NMN oral administration group), and a group to which the β-NMN-containing external preparation was transdermally administered (NMN transdermal and oral administration group). The group orally administrated was used as a group transdermally administered the solvent of the external preparation (control group). At the time of transdermal administration, a site applied the β-NMN-containing external preparation or solvent was set in advance, and application was performed to the same site each time. A day performed this group dividing was was considered day 0 of administration, and from the next day, the β-NMN solution or was orally administered, and furthermore, the solvent or β-NMN-containing external preparation was transdermally administered to the guinea pigs of each group once a day for 42 days. In the oral administration, the β-NMN solution was administered at a dosage of β-NMN of 500 mg/kg body weight, and in the transdermal administration, 0.05 mL of the β-NMN-containing external preparation or solvent was applied per application site.

(Ultraviolet Irradiation)

Ultraviole tirradiation was performed on the guinea pigs in each group a total of three times, on a day after 15 days of the administration (first irradiation day), and on days after 2 and 4 days therefrom. Ultraviolet irradiation of the guinea pigs was performed as the same manner in Example 1. An irradiation time was set to the minimum erythema dose (12 minutes and 15 seconds). On the day of the ultraviolet irradiation, the β-NMN-containing external preparation or solvent was administered after the irradiation.

(Measurement of Pigmentation)

L values (brightness) of the skin of the ultraviolet irradiation site of each guinea pig were measured as the same manner in Example 1 on the first irradiation day, and on a day after 28 days from the first irradiation. On the first irradiation day, L values were measured before the irradiation, and on a day after 28 days from the first irradiation, L values were measured in the morning.

Each guinea pig was shaved as the same manner in Example 1.

ΔL values were calculated from the measured L value as the same manner in Example 1.

(Photographing)

One example of each group was photographed after measurement of the L values by a digital camera.

(Results)

Figure 2:
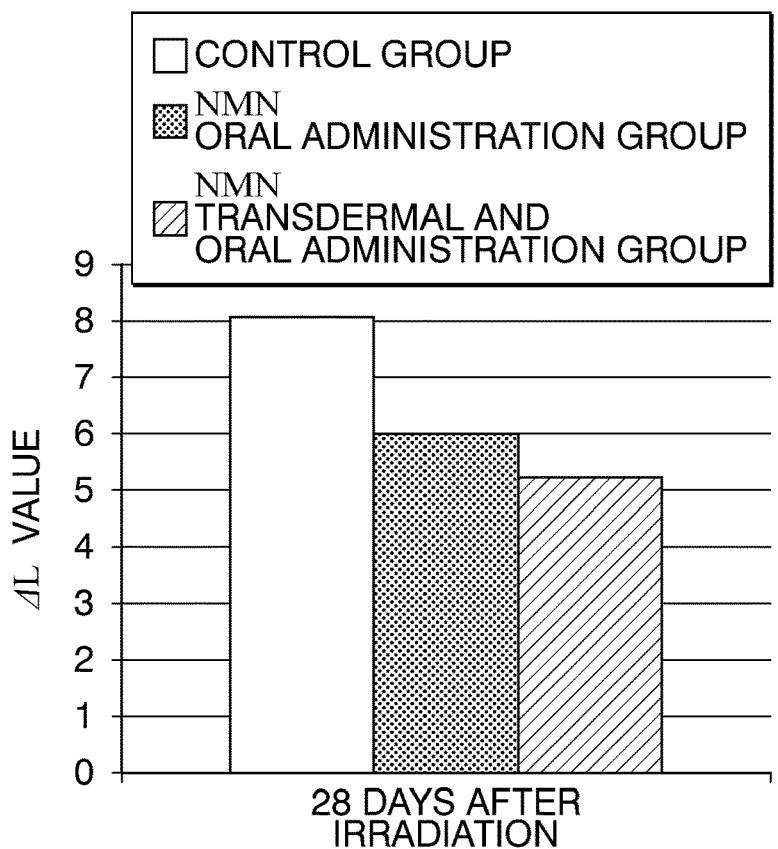
FIG. 2 is a graph showing an amount of change in an L value (ΔL value) at an ultraviolet irradiation site for each guinea pig in a group to which only β-NMN is orally administered (NMN oral administration group), a group to which β-NMN is transdermally and orally administered (NMN transdermal and oral administration group), and a group to which a solvent is transdermally administered (control group) in Example 2.

The ΔL values measured of each group are shown in FIG. 2. In the NMN oral administration group and the NMN transdermal & oral administration group, the ΔL value of the ultraviolet radiation site was checked to be smaller in the NMN group than that in the control group. In the NMN transdermal & oral administration group, the ΔL value of the site was checked to be smaller than that of the NMN oral administration group. More specifically, the ΔL value of the control group was 8.07, the ΔL value of the NMN oral administration group was 6.01, and the ΔL value of the NMN transdermal & oral administration group was 5.20. Compared with the control group, pigmentation was inhibited by orally administering NMN, and pigmentation was further inhibited by adding transdermal administration in addition to oral administration than in the case of only oral administration. Based on these results, it was confirmed that pigmentation due to ultraviolet irradiation can be further inhibited by applying β-NMN to the skin surface in addition to oral administration of β-NMN.

The invention claimed is:

1. A method for inhibiting skin pigmentation in a human or an animal other than a human, comprising:
   orally administering a pigmentation inhibitor to the human or the animal other than a human,
   wherein the pigmentation inhibitor comprises as an active ingredient, β-nicotinamide mononucleotide or a pharmaceutically acceptable salt thereof or a solvate thereof.

2. The method according to claim 1, wherein the animal other than a human is a mammal other than a human.

3. The method according to claim 1, wherein
   the pigmentation inhibitor further comprises at least one material selected from the group consisting of a vitamin, a carbohydrate, a protein, a lipid, a dietary fiber, and a fruit juice.

* * * * *